United States Patent [19]

Parvin et al.

[11] Patent Number: 5,671,086

[45] Date of Patent: Sep. 23, 1997

[54] METHOD AND APPARATUS FOR ACCURATELY MANIPULATING AN OBJECT DURING MICROELECTROPHORESIS

[75] Inventors: Bahram A. Parvin, Hercules; Marcos F. Maestre; Richard H. Fish, both of Berkeley; William E. Johnston, Kensington, all of Calif.

[73] Assignee: The Regents, University of California, Oakland, Calif.

[21] Appl. No.: 423,969

[22] Filed: Apr. 18, 1995

[51] Int. Cl.$^6$ .................... G02B 21/26; G02B 21/00; G02B 21/36; G01N 21/01

[52] U.S. Cl. .................... 359/391; 359/395; 359/393; 359/398; 359/368; 359/369; 250/311

[58] Field of Search .................... 359/391, 395, 359/393, 398, 397, 368, 369; 250/311

[56] References Cited

U.S. PATENT DOCUMENTS

| | | | |
|---|---|---|---|
| 4,046,667 | 9/1977 | Goetz | 204/299 R |
| 4,911,817 | 3/1990 | Kindlmann | 204/299 R |
| 4,997,266 | 3/1991 | Mitchell | 359/398 |
| 5,106,468 | 4/1992 | Chimenti | 204/180.1 |
| 5,108,567 | 4/1992 | Kolble | 204/180 |
| 5,192,503 | 3/1993 | McGrath et al. | 359/398 |
| 5,306,467 | 4/1994 | Douglas-Hamilton et al. | 359/398 |
| 5,436,129 | 7/1995 | Stapleton | 435/6 |
| 5,516,698 | 5/1996 | Beg et al. | 436/89 |

OTHER PUBLICATIONS

Fish, Richard et al., "Bioorganometallic Chemistry: The Reactions of a ($\eta^5$–Pentamethylcyclopentadienyl)rhodium Aqua Complex with Nucleobases, Nucleosides, Nucleotides, and Oligonucleotides" *Nato Advanced Research Workshop* pp. 1–15 (Aug. 1994).

Parvin, B. et al., "Tracking of Tubular Objects for Scientific Applications" *Imaging Technologies Group of Lawrence Berkeley Laboratory* pp. 1–7.

Primary Examiner—Paul M. Dzierzynski
Assistant Examiner—Mohammad Y. Sikder
Attorney, Agent, or Firm—Paul R. Martin

[57] ABSTRACT

An apparatus using electrophoresis provides accurate manipulation of an object on a microscope stage for further manipulations add reactions. The present invention also provides an inexpensive and easily accessible means to move an object without damage to the object. A plurality of electrodes are coupled to the stage in an array whereby the electrode array allows for distinct manipulations of the electric field for accurate manipulations of the object. There is an electrode array control coupled to the plurality of electrodes for manipulating the electric field. In an alternative embodiment, a chamber is provided on the stage to hold the object. The plurality of electrodes are positioned in the chamber, and the chamber is filled with fluid. The system can be automated using visual servoing, which manipulates the control parameters, i.e., x, y stage, applying the field, etc., after extracting the significant features directly from image data. Visual servoing includes an imaging device and computer system to determine the location of the object. A second stage having a plurality of tubes positioned on top of the second stage, can be accurately positioned by visual servoing so that one end of one of the plurality of tubes surrounds at least part of the object on the first stage.

12 Claims, 7 Drawing Sheets

METHOD AND APPARATUS FOR ACCURATELY MANIPULATING AN OBJECT DURING MICROELECTROPHORESIS

ORIGIN OF THE INVENTION

This invention was made with Government support under Contract No. DE-AC03-76SF00098 awarded by the U.S. Department of Energy, Office of Scientific Computing, under Grant No. AIO8427-25 awarded by the National Institute of Health and under a Laboratory Directed Research and Development grant awarded by the Director of Lawrence Berkeley Laboratory. The Government has certain rights in this invention.

BACKGROUND OF THE INVENTION

1. Field of the Invention

This invention relates to moving an object on a microscope stage and more particularly to providing a novel use of electrophoresis for accurate manipulation of a molecular sized object for further manipulations and reactions.

2. Previous Art

In order to move a microscopic object to a predetermined position for a specific use or study, scientists must physically push or pull the object. For example, in the microinjection of cells, scientists use small tools under an imaging microscope to push the cell into the desired orientation and position. This is done manually, either with or without the aid of a micromanipulator. However, physically touching the object of study and manipulation can cause damage to the object, thereby wasting precious resources, increasing the cost of an experiment and the time necessary to complete it. Additionally, this method cannot be employed for molecular sized objects.

Researchers use the tip of an atomic force microscope (AFM) to push molecular sized objects on a microscope stage. For example, in 1990, the International Business Machines Corporation released a photograph of xenon atoms on a nickel surface spelling "IBM." These scientists used a scanning tunneling microscope (a precursor to the AFM) to push the atoms into the desired positions. 344 NATURE 524 (1990). However, the AFM cannot be used for manipulations for sectioning of DNA molecules and for further manipulations for the purpose of capturing the fragment of sectioned DNA.

In most laboratories, DNA molecules are not manipulated with accuracy. For example, a common technique for manipulating bulk amounts of DNA is electrophoresis. Electrophoresis is the motion of charged particles through a relatively stationary liquid or gel, under the influence of an applied electric field provided, in general, by immersed electrodes. Electrophoresis is used to sort fragments of DNA by size, for example, after the DNA has been cut with restriction enzymes, in sequencing DNA (by labeling nucleotides and separating the labeled DNA fragments by size), and capturing desired fragments of DNA by running them out of gel pieces and into containers useful for further manipulations. However, current methods of electrophoresis only run DNA in bulk. Current methods cannot accurately manipulate single DNA molecules for additional reactions while the molecules are under electrophoresis.

Dr. S. Chu at Princeton University, developed "optical trapping." Optical trapping uses laser pressure to move a single object without physically touching the object. However, this technique cannot move DNA or equivalently sized molecular objects on a microscope stage. This method can only carry an object whose optical cross-section is on the order of the wavelength of light, about 5,000 Å. Chu, *Laser Manipulation of Atoms and Particles*, 253 SCIENCE No. 5022, at 861 (Aug. 23, 1991).

Object detection and tracking has been a major area of research in the computer vision community. Typical applications include target tracking, autonomous navigation, process control, and scientific data analysis. Most of the previous papers in the vision literature aim at either detection or tracking objects of interest in the scene. However, very little attention has been given to combining these techniques for real world applications. From this perspective, several papers have dealt with detection of ribbons, generalized cones, and more recently, generalized tube model. A brief review follows.

Huertas, et al., developed a system to detect runways in aerial images (ribbons). They used a hypothesis-and-verification strategy to achieve their goal. The initial hypotheses are obtained by detecting peaks in the histogram of edge orientation images. The underlying idea is that such manmade objects will have a global orientation. Local hypothesis formation is initiated by detecting anti-parallel segments from low level edge information. These isolated anti-parallel segments, referred to a apars, are then joined based on their continuity, collinearity, and consistency with global orientation and certain knowledge about airport engineering. Huertas, Cole and Nevatia, *Detecting Runways in Complex Airport Scenes*, 51 (2) COMPUTER VISIONS, GRAPHICS, AND IMAGE PROCESSING 107 (August 1990).

Lowe developed a system called SCERPO, the goal of which is to recognize and locate 3D rigid parts from a single gray-scale image. High level features such as instances of collinearity, end-point proximity, and parallelism are built based on straight lines formed by low level processes. These features are then combined into larger, more complex structures, in a stepwise fashion. Finally, the structure patterns are used to limit the search space by hypothesizing the position of the part, which is verified by back projecting on the edge data. Lowe, *Three-Dimensional Object Recognition From Single Two-Dimensional Images*, 31 ARTIFICIAL INTELLIGENCE 355 (1987).

Brooks developed a system called ACRONYM. A typical application of this system is to identify airplanes in aerial images of airfields. In this system, objects are modeled as subpart hierarchies in terms of generalized cones (which are two dimensional shapes, and consist of a cross section swept across a spine). Brocks, *Model-Based Three-Dimensional Interpretations of Two-Dimensional Images*, 5(2) IEEE TRANSACTIONS ON PATTERN ANALYSIS AND MACHINE INTELLIGENCE 140 (1983).

More recently, Huang and Stockman introduced the generalized tube model, where the tube model is locally similar to GC. Their tube model combines contour and shading-based techniques in a unique fashion. The contour information is used to hypothesize local tubes that are verified by matching their shading-based techniques in a unique fashion. The contour information is used to hypothesize local tubes that are verified by matching their shading properties with dynamically generated optimal filters. The recognition step then sweeps across locally verified tubes using a best fit constraint. Huang and Stockman, *Generalized Tube Model: Recognizing 3d Elongated Objects from 2d Intensity Images*, PROCEEDING OF THE CONFERENCE ON COMPUTER VISION AND PATTERN RECOGNITION 104 (New York, June 1993).

In the context of tracking, most of the previous work is based on a variation of the Snake model. This model assumes that an initial contour, defined interactively, is placed near the desired boundaries by means of a closed polygon or spline. This initial contour is then refined using a cost function that integrates internal and external energies, i.e., $$E_{snake} = \alpha E_{external} + E_{internal} \quad \text{(Formula 1)}$$

where the external energy is measured by image forces such as gradients or zero crossings, and the internal energy is measured by the amount that the contour is being stretched or bent. Kass, Witkin and Terzopoulos, *Snakes: Active Contour Models*, PROCEEDINGS OF THE IEEE INTERNATIONAL CONFERENCE ON COMPUTER VISION 259 (London, England, June 1987).

Several refinement strategies based on relaxation, variational calculus, and dynamic programming have been proposed. The relaxation technique optimizes a local cost functions, where the other two aim at global optimization of the cost function. Williams and Shah, *A Fast Algorithm for Active Contours and Curvature Estimation*, 51(1) COMPUTER VISION, GRAPHICS, AND IMAGE PROCESSING 14 (1992). There are some numerical anomalies in the variational approach that can be side-stepped by the other two techniques. Kass, Witkin and Terzopoulos, *Snakes: Active Contour Models*, PROCEEDINGS OF THE IEEE INTERNATIONAL CONFERENCE ON COMPUTER VISION 259 (London, England, June 1987); Leymarie and Levin, Tracking Deformable Objects in the Plane Using an Active Contour Model, 15 IEEE TRANSACTION ON PATTERN ANALYSIS AND MACHINE INTELLIGENCE 617 (1993). In general, the Snake model assumes that the initial contour need not be placed near the desired boundaries[1] and the model is capable of deforming its initial contour into a state where the cost function is optimized. Amini, Tehrani, and Weymouth, *Using Dynamic Programming for Minimizing the Energy of Active Contours in the Presence of Hard Constraints*, PROCEEDINGS OF THE IEEE INTERNATIONAL CONFERENCE ON COMPUTER VISION 95 (Tampa, Fla., 1988).

[1] In the sense that the scope of the search may include the entire scene.

As stated above, these techniques of detection an tracking have not been combined for manipulating single DNA molecules.

What is needed is a means for moving a single molecule on a microscope stage in an accurate manner for subsequent reactions, for example sectioning and capture of the sectioned segments.

SUMMARY OF THE INVENTION

It is an object of this invention to provide a means for moving a single molecule on a microscope stage in an accurate manner for further manipulations and reactions.

In accordance with the above object and those that will be mentioned and will become apparent below, the apparatus for manipulation of an object on a microscope stage in accordance with this invention comprises:

An apparatus for manipulation of an object on a microscope stage comprising:
   a microscope having a stage; and
   a plurality of electrodes coupled to the stage for creating an electric field across the stage, the electric field having one or more changeable parameters, whereby changing the electric field causes the object on the stage to move from a first position to a preferred second position.

In a preferred embodiment, the plurality of electrodes are coupled to the stage in an array for allowing distinct manipulations of the electric field for accurate manipulations of the object. The term electrode array is intended to mean and include the position of the plurality of electrodes, not necessarily in an orderly arrangement or rectangular matrix.

The above mentioned preferred embodiment further comprises an electrode array control coupled to the plurality of electrodes for manipulating the electric field.

Another preferred embodiment comprises a chamber on the stage to hold the object, the plurality of electrodes being coupled to the chamber, and the chamber being filled with a fluid.

Another preferred embodiment includes automating the system by providing an imaging device and at least one processing unit.

It is an advantage of this invention to provide a means for moving a single molecule on a microscope stage in an accurate manner for further manipulations and reactions.

BRIEF DESCRIPTION OF THE DRAWING

For a further understanding of the objects and advantages of the present invention, reference should be had to the following detailed description, taken in conjunction with the accompanying Drawing, in which like parts are given like reference numerals and wherein.

DETAILED DESCRIPTION OF THE INVENTION

The invention will now be described with respect to FIG. 1, which illustrates the method and apparatus for accurate manipulation of an object 10 on a microscope stage 12. All elements of the invention and solutions disclosed are those typically found in a molecular biology laboratory, or can be ordered through a laboratory supply catalogue. First, a microscope 14 having a stage 12 is provided. This can be any type of imaging microscope, including inversion and immersion microscopes. A mechanical stage control 16 is used for manipulating the stage 12 in the Z direction, i.e., up and down for focusing. Directions X and Y are used for moving the stage 12 within the plane of the top surface of the stage 12.

A plurality of electrodes are coupled to the stage 12 for creating an electric field across the stage 12. The electric field comprises changeable parameters, including, but not limited to, being on or off, direction and intensity. The plurality of electrodes of the present invention are coupled to the stage in an array for allowing distinct manipulations of the electric field for accurate manipulations of the object 10. The term electrode array is intended to mean and include the position of the plurality of electrodes, not necessarily in an orderly arrangement or rectangular matrix. There are many possible combinations of coupling the plurality of electrodes to the stage 12 that allow for accurate manipulation of the object 10. The electrode array of this invention includes all possible geometric configurations. The particular electrode array chosen will depend on how the object 10 is to be manipulated. For example, as shown in FIG. 1, the negative electrode may consist of a single bar 18, and the positive electrode may consist of multiple tips 20. An electric field flows from a negative to a positive electrode. This electrode array will allow for finer detail in manipulation of the object 10 near the positive electrode tips 20 rather than near the single negative electrode 18.

An electrode array control 22 is provided for manipulating the electric field. The specific type of electrode array control 22 will depend on the electrode array used in the invention. Models, descriptions, and functions of electrode array controls are given in laboratory supply catalogues. The electrode array control 22 is coupled to the plurality of electrodes for accurate manipulation of the electric field.

A method for manipulating an object 10 in accordance with the above example comprises the steps of placing the object 10 on the stage 12, the object 10 being located at a first position. The electrode array control 22 is manipulated, creating a change in the electric field, whereby changing the electric field causes the object 10 on the stage 12 to move from the first position to a preferred second position. For example, in some instances, simply turning on the electric field will move the object. In other instances, the electrode array control 22 is manipulated in a specific manner, and the object 10 is moved to a specific position, i.e., in a similar manner that one draws with the popular toy "Etch-A-Sketch™."

Two possible methods of manipulating the electric field include manual control of the electrode array control 22 and automatic calibration and control of the electrode array control 22.

Manual control entails the scientist to physically adjust the electrode array control 22 while watching the effects of the electric field on the object 10 through the microscope 14.

Figure 1:
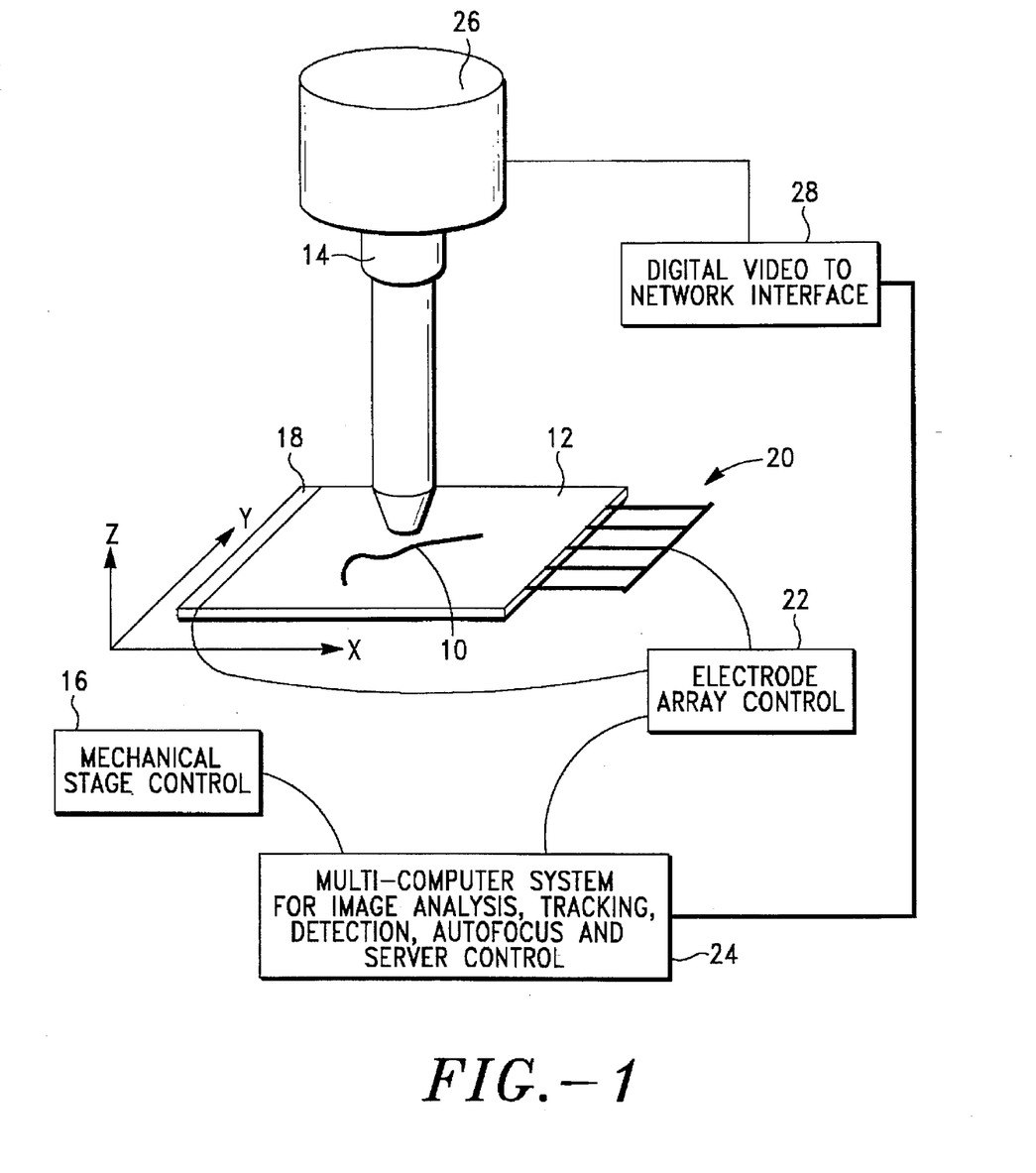
FIG. 1 is a simplified view of an embodiment of the invention, wherein a plurality of electrodes are coupled to the microscope stage.

Also illustrated in FIG. 1 is a visual servomechanism for automatic calibration and control of the system to manipulate an object on a microscope stage. The visual servomechanism includes a multi-computer system 24, or a processing unit, and an imaging device 26 (for example, a video camera). The processing unit is electrically connected to the electrode array control and the mechanical stage control, and the electrode array control and the mechanical stage control are responsive to the processing unit. A single, very fast processing unit including appropriate hardware specialized for sensing and controlling its environment (for example, the electric field and stage control) may be used. Alternatively, multiple interconnected specialized systems where separate processors are assigned specific parts of the overall task (for example, video stream analysis, tracking objects, electric field sensor and controller, etc.) may be used.

The imaging device 26 is electrically connected to the microscope 14 for creating an image of the stage 12. There is also a digital video to network interface 28 to transmit the image of the stage 12 to the multi-computer system 24. The multi-computer system 24 receives and uses this image to detect the first position of the object 10 on the stage 12. The multi-computer system 24 then detects the preferred second position of the object, determines how to change the electrode array control for changing the electric field to move the object from the first position to the preferred second position and changes the electrode array control, whereby the electric field moves the object from the first position to the preferred second position.

The multi-computer system 24 also performs video stream analysis (auto focus control (z), stage control (x,y) and tracking calculations) and is a network disk array (multimedia storage).

Tracking of Tubular Objects for Scientific Applications

The object 10 is automatically detected by the multi-computer system 24 from the image obtained through the imaging device 26. Detecting the position of the object 10 in the image is a specific tracking problem for scientific applications. The main thrust in such scientific applications is either to gain new insights about the behavior of an object or to establish-and-verify certain hypotheses. The domain is constrained to objects that are elongated and maintain parallel symmetries. These objects are referred to as "tubular objects" that may or may not be terminated at both ends. In addition to man-made objects, such objects occur abundantly in nature: coronary arteries, bacteria, chromosomes and macro structures in human lungs.

The present invention detects, tracks and performs shape representation of tubular objects. The approach is through an implementation that detects and tracks DNA molecules (a class of tubular objects) obtained through epi-fluorescence microscopy. An epi-fluorescence microscope is a typical scientific imaging device that operates at the extreme limit of the optical system and the photo conversion limits of the receptor system.

The main novelty of the system lies in the use of high level geometric features for object detection and the subsequent use of this information in the localization of individual molecules, followed by the re-use of this information for tracking. High level constructs are extracted from incomplete low level information, and then used to refine and complete the low level results. In the application domain, the high level constructs, or the most perceptually significant features, are ribbon-like structures defined by a collection of substructures called U-shapes and anti-parallel segments. These isolated segments are grouped with respect to the object model where a coarse description of the molecule is obtained in terms of a bounding polygon. This global representation is then refined using local pixel activities. The refinement is achieved through dynamic programming that ensures global optimality. The refined contour is then projected and updated in every consecutive frame. Furthermore, to facilitate subsequent quantitative analysis, the refined contour is represented by its axis of symmetry. This representation is then used to study the motion and mechanical properties of the molecules. The general architecture of this system is shown in FIG. 2, and consists of detection, tracking, and shape representation subsystems.

The system operates on the 2D flat world. Its similarity to ACRONYM is in the use of an object model to drive the search process. And its commonality with Huertas's work is in the use of high level features for grouping. Still, the present formulation for the particular application is unique in terms of the consistent labeling of the high level features. The detection phase of the system provides a coarse approximation, in terms of a bounding polygon, for each molecule. The fact that this description is very close to the actual boundary of the molecule, and that the motion of each molecule between consecutive frames is only several pixels, has enabled us to design a simple tracking mechanism that significantly limits the scope of search during refinement. Furthermore, our cost function is simpler than the traditional Snake model; it does not rely on the rectangular tessellation of the pixel layout to compute the corresponding energy function, and it eliminates the scaling parameters for the internal and external forces.

3. Detection Subsystem

Figure 2:
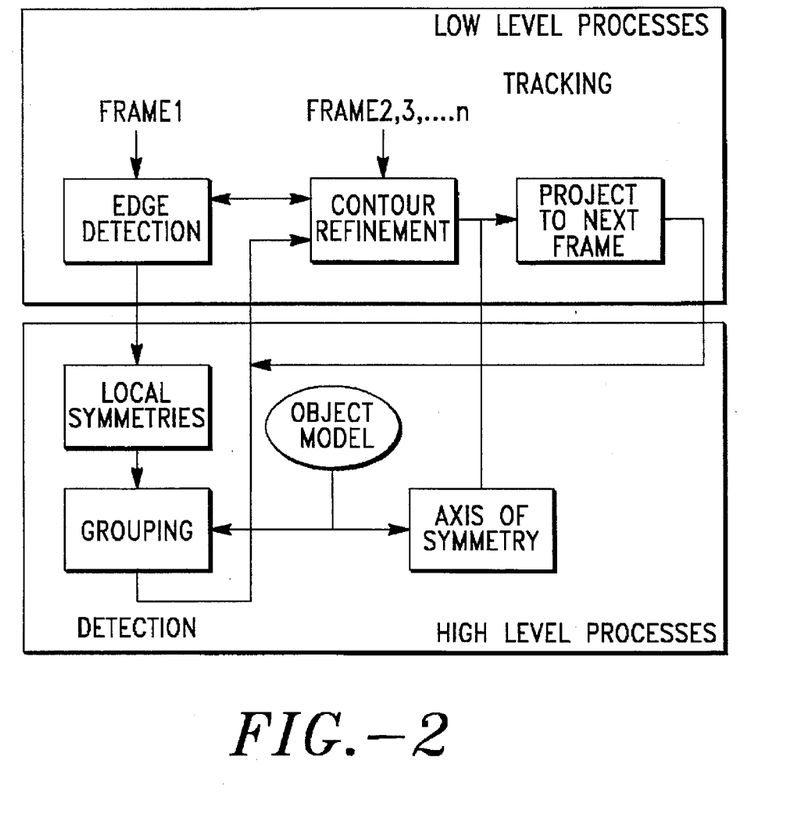
FIG. 2 is the general architecture of the tracking system.

In this section the different components of the detection process are summarized as shown in FIG. 2, and intermediate results for each important step of the process are presented. The edge detection is based on Canny's approach, which is inherently a gradient operator. Canny, *A Computational Approach to Edge Detection*, 8(6) IEEE TRANSACTIONS ON PATTERN ANALYSIS AND MACHINE INTELLIGENCE 679 (November 1986). The resulting edges are linked, curve segments are extracted, and polygon representation of these curve segments are obtained. The edge gradient and directions are computed at a coarse and fine scale. The coarse scale information is used in the detection phase for better noise immunity, and the fine scale information is used in the tracking phase for better localization. In general, due to noise and variation in contrast, the edge detection technique produces broken and undesirable curve segments. The objective is to group these curve segments such that the individual objects can be extracted from background. This is accomplished by representing curve segments by richer representations which are referred to as "ribbons" in the computer vision literature. A ribbon is a polygon formed by a set of anti-parallel regiments of U-shapes. In Brooks' definition, a ribbon is a two dimensional analog of a generalized cone. These local ribbons correspond to local symmetries that provide the foundation for grouping them into a larger structure based on a suitable object model. The ribbon representation is difficult to compute, but it simplifies the process of high level reasoning.

3.1 Local Symmetries

Local symmetries are identified either from U-shapes or antiparallel segments. U-shapes correspond to the ends of a molecule or points of maximum curvature, and antiparallel segments correspond to the main body of the molecule.

A U-shape is a collection of connected line segments whose total accumulation of the angles between adjoining segments is approximately 180 degrees. There are several ways to extract U-shapes from polygon approximations of curve segments. One way of doing this is by summing the angles $\theta_i$ between adjacent line segments $l_i$ and $l_j$ at multiple scales, where scale refers to the number of line segments that are used in the computational process. The alternative approach is to search for line segments with opposite directions in the same curve segment. Both of these approaches can generate multiple U-shapes. This is resolved by imposing the constraint that a U-shape should be formed with minimum number of consecutive line segments.

An anti-parallel line is a pair of parallel line segments with opposite directions that can be projected onto one another. This construct is sometime referred to as an "apars" in the literature. Huertas, Cole and Nevatia, *Detecting Runways in Complex Airport Scenes*, 51(2) COMPUTER VISION, GRAPHICS, AND IMAGE PROCESSING 107 (August 1990). There are two types of anti-parallel lines in our system. These are the anti-parallel lines formed by line segments that belong to the same curve segment, and the anti-parallel lines that are formed by the line segments from different curve segments. This is due to the fact that the anti-parallels formed between two different curve segments may not correspond to a single object. If the anti-parallel segments occur between different pieces of the same curve segments then the search process (for anti-parallel) is initiated from the position of the U-shape. On the other hand, if an anti-parallel segment occurs between different curve segments, then they can only be discovered by scanning normal to a line segment and forming a correspondence histogram.

3.2 Grouping

We expressed the grouping problem as a function of three entities:

DNA=Group (features, object model, geometric constraints)

In this formulation, features correspond to nodes with labels, and some attributes where a label can be either a U-shape or anti-parallel, and the attributes that encode its invariant geometric measures. The object model represents the relationship between the nodes of an idealized DNA model as described by U-shapes and anti-parallels. The geometric constraints encode the rules by which the nodes can be linked together. The goal of the grouping is to connect high level features, represented as nodes of a disconnected graph, in such a way that labeling of these nodes remains consistent with respect to the object model subject to the geometric constraints. In this approach, the grouping function is self-correcting since a single node might be mislabeled due to various perturbations in the lower level processes, and errors can be corrected and the grouping process continues. The following is a detailed description of the object model, geometric constraints, and the grouping strategy to link a disconnected graph in a coherent fashion.

3.2.1 DNA Object Model

The object model is based on a priori knowledge about the occurrence of objects in an image that may include shape, texture and context. A DNA molecule is distinguished by its symmetric-elongated shape with the following features:

1. Every DNA has two U-shapes, one at each end;
2. There are anti parallel lines between these two U-shapes;
3. The variation in the width of a DNA is small; and
4. If the U-shapes and anti-parallels are represented as nodes, and the relationships between them as a link, then the links must be consistent. This is referred to as "Link Consistency" that will be explained later in more detail.

Figure 3:
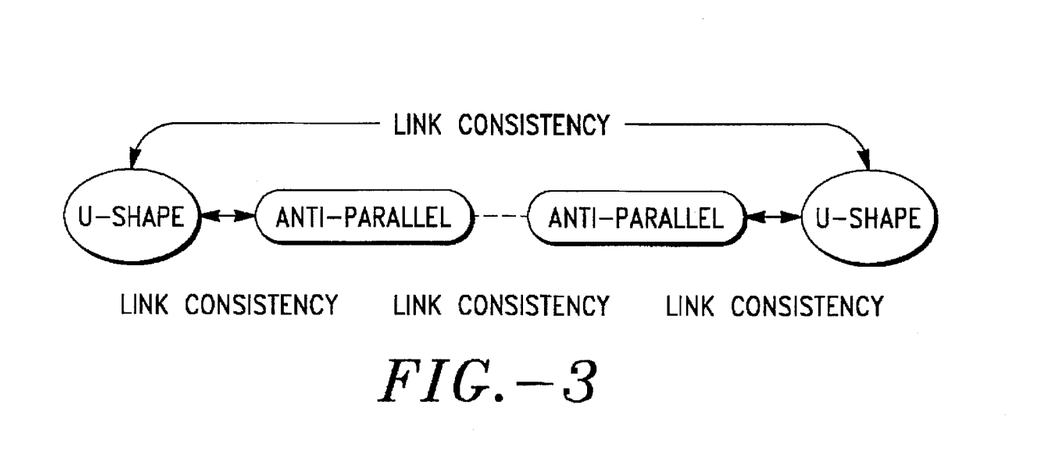
FIG. 3 is a DNA model of the tracking system.

The relationship between the nodes of a DNA object is represented as a graph as shown in FIG. 3. As pointed out, the significant characteristic of DNA molecules is their symmetric shape, and these symmetries can be localized by detection of ribbon-like structures that are computed through incremental coercion of the high level representation.

3.2.2 Geometric Constraints

The goal of the grouping process is to connect high level features in such way that labeling of these features remains consistent with the geometric constraints of the object model. These geometric constraints can be described as:

1. Multiple-overlapping ribbons cannot be formed by the same line segments:
    This constraint is implied by the DNA model, and is used to filter out irrelevant high level features and reduce the search space.
2. Ribbons share a common curve segment:

Ribbons that are formed by the same curve segment are likely to belong to the same object, and hence, they can be included in the same group.

3. Ribbons are collinear with each other; and
4. Ribbons have uniform width.

These geometric constraints, together with the object model and high level features, establish the basis for the grouping process.

Geometric Grouping

This step of the computational process attempts to assign a tag (unique ID) to each DNA object. This is accomplished by utilizing the geometric constraints in a stepwise fashion. However, the labeling consistency constraint defined by the model may not be guaranteed in this process. Hence, a set of verification steps are required to ensure the labeling consistency.

1. U-shape consistency verification:

Every DNA has only two U-shapes and these are located at its ends. If a set of curve segments form more than two U-shapes, then some of these U-shapes must be erroneous. We distinguish these false U-shapes by a width property that is inconsistent with the width of other U-shapes.

2. Linking consistency checking:

The two U-shapes must be connected by anti-parallel lines. We call this the "link consistency constraint" which is also used to remove false U-shapes.

Figure 4:
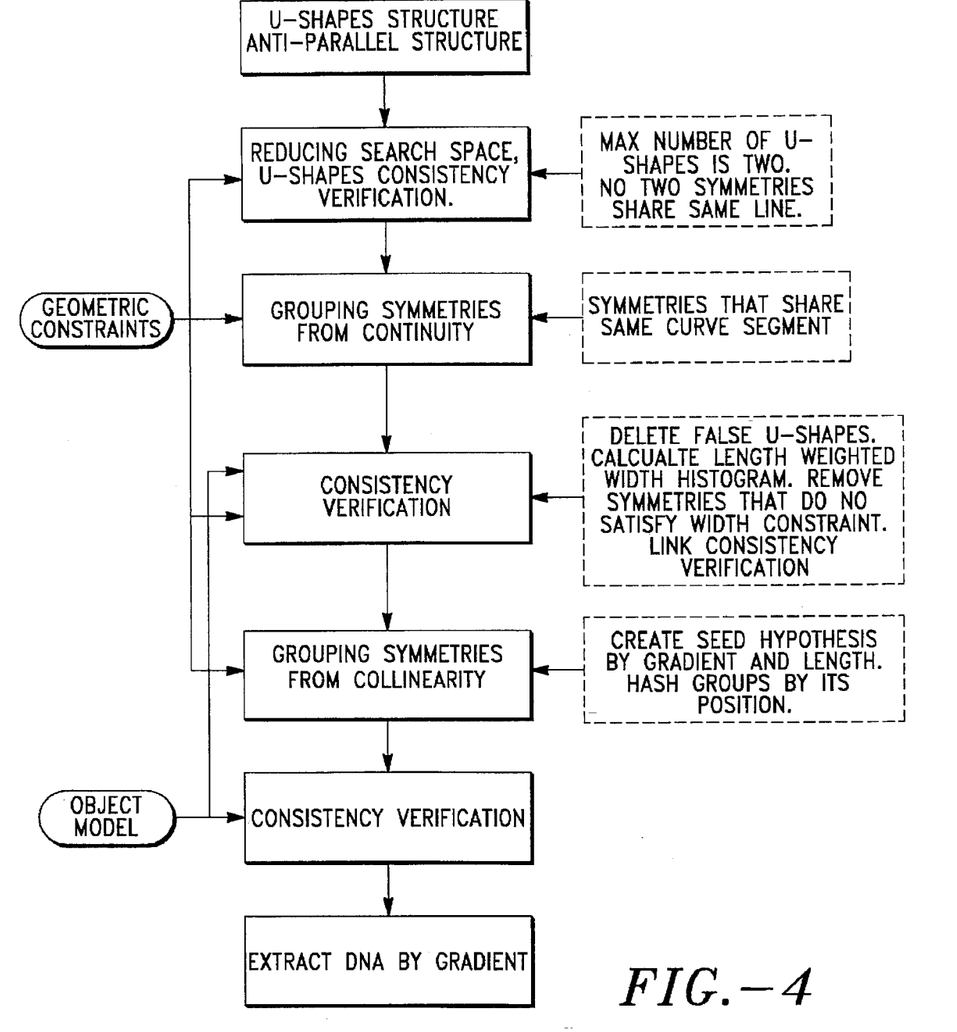
FIG. 4 is the grouping process of the tracking system.
Figure 5:
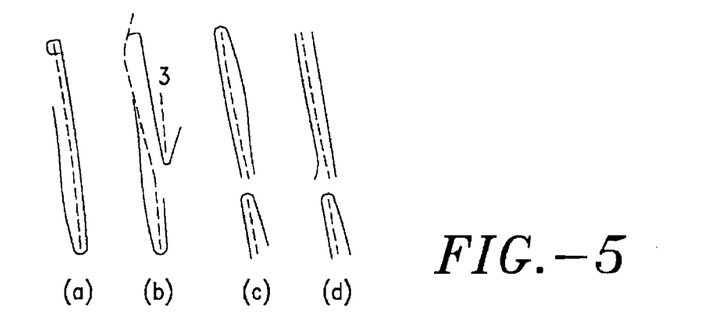
FIG. 5 is the link inconsistency in the tracking system.

FIG. 4 shows various steps in the grouping process, and a list of illegal junctions is shown in FIG. 5. These link inconsistencies are: (a) T junction; (b) Concave boundary between 1 & 3; (c) Two co-directional U-shapes; (d) an inconsistent U-shape and anti-parallel.

4. Tracking Subsystem

Extraction of closed contours that correspond to real object boundaries has been a major area of research in low level vision. As already pointed out, this is a difficult and complex task in the absence of any high level constraints. In some cases, high level constraints can be entered interactively. But, regardless of whether these high level constraints are incorporated interactively or computed automatically, some form of refinements is needed. The present invention formulates the refinement process as a cost function that encodes both the low level and high level constraints in a unique fashion. The actual optimization of the cost function is achieved via dynamic programming, which ensures global optimality in the search process. In this context, the system allows a course description, expressed by a bounding polygon, to snap back into the original contour and construct a refined representation. The refined contour is then convolved with a Gaussian kernel and projected upon each subsequent frame so that the tracking is advanced.

4.1 Cost Function

The cost function should encode the desirable properties of the refined contour. In the formulation, this is defined in terms of high and low level feature activities. The low level features refer to pixel level information such as local edge magnitude and direction. The high level features refer to the measurements that can be made from the bounding polygon. In this system, the high level constraints (bounding polygon) affect the contour refinement in two ways. The first one is a geometric constraint, which we will discuss later, and the second one is by limiting the scope of the search. This is accomplished by smoothing the initial polygon with a Gaussian kernel and bounding the refined contour to lie in a small neighborhood as defined by the normal lines to the smooth curve.

Figure 6:
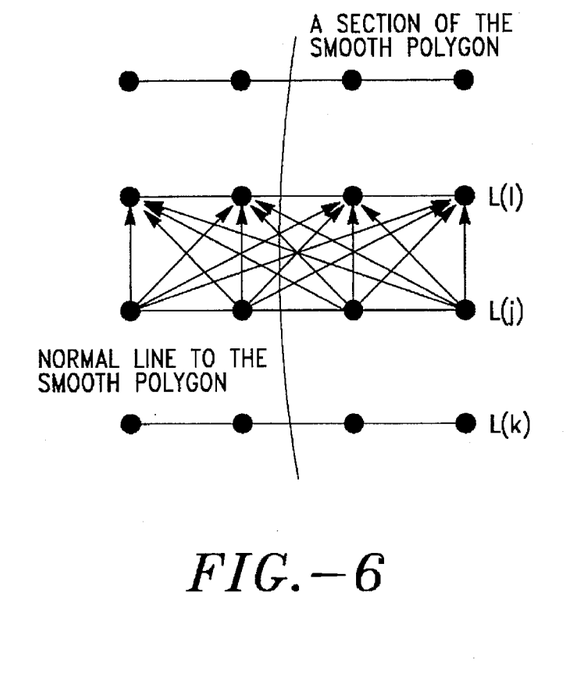
FIG. 6 represents possible paths for each point on a normal line segment in the tracking system.

Conceptually, each point on the refined contour should have high gradient and good continuity with both the low and high level features. This is reflected in the cost function in terms of making a decision for a particular path. The cost function indicates the accumulation of making a decision to link two points from two consecutive normal line segments as shown in FIG. 6. Let:

1. $g_i$ be the gradient magnitude for a point $p_i$ on line $L_i$,
2. $\theta_i$ be the direction of the gradient at location $p_i$
3. $\Delta\theta_{ij}$ be the difference between the direction of gradient for points $p_i$ and $p_j$,
4. $\gamma_i$ be the angular difference between local edge direction and local direction of high level constraint,
5. $\eta_{ij}$ be the angle between the gradient direction at point $p_i$ and the vector connecting point $p_j$ to $p_i$,
6. $w_{ij}$ be the distance between points $p_i$ and $p_j$ located on two consecutive normal line segments, and
7. $\alpha_{ij}$ be the directional deviation between two consecutive points defined as MAX ($\Delta\theta_{ij}$, $\eta_{ij}$).

The cost function is formulated in such a way that the gradient is maximum, directional differences are small and the deviation for a particular path from the bounding polygon (high level constraint) is also small. One way to express such a cost function is as follows:

$$MAX_{i,j,k} \sum_k \sum_i \sum_j \frac{1}{w_{ij}} g_i e^{-\tan(\frac{\gamma_i}{s})} \cos(\alpha_{ij}) \quad \text{(Formula 2)}$$

Where k is the length of the contour; i and j are the pixel location on normal line to the smooth polygon. This formulation allows the curve to expand and shrink as necessary. Furthermore, by expressing the cost function as a product of internal and external energies, as opposed to the sum in Formula (1), we have eliminated scaling coefficients that are used in the Snake formulation. The above cost function is optimized with the dynamic programming principle.

5. Shape Representation

The system of the present invention aims to detect and track DNA over a sequence of images. The shape of DNA is represented in such a way that the significant shape measures are captured. This is another step in the data reduction process that is used to visualize the temporal motion of the object. The simplest method to represent the shape of a DNA molecule is by its medal axis, which is sometimes referred to as "thinning." Rosenfeld, *Axial Representations of Shape*, 2(33) COMPUTER VISION, GRAPHICS, AND IMAGE PROCESSING 156 (1986). Yet, most thinning techniques ignore high level information and fail to generate desired results. Here, a simple technique is proposed that is adequate for the present application domain.

The present approach to thinning is to use the high level information about the shape of DNA to guide extraction of medial axes. This is accomplished by utilizing the end points of a DNA to partition the corresponding contour into two halves where the medial axis can be computed directly. A brief description for localizing the end-points of a molecule during tracking is followed.

5.1 Locating the End Points

Figure 7:
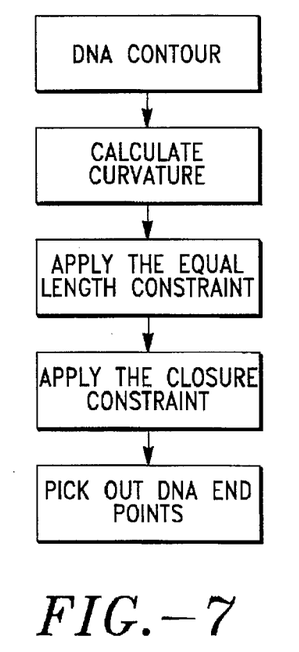
FIG. 7 is the process of finding the end points of a molecule in the tracking system.

From a geometric point of view, under ideal conditions, the end points of DNA correspond to the location of maximum curvature along the contour. Yet, contour information is generally noisy, as a result the positions of maximum curvatures do not necessarily correspond to the end points of DNA. In other words, curvature information by itself is not a sufficient constraint. To resolve this problem, we add equal length and closure constraints as two additional constraints. Each pair of hypotheses, corresponding to the curvature peaks, divides the length of the contour into two halves, where equal length and closure constraints are applied. Each of these steps, i.e., computation of curvature and application of various constraints, are designed to reduce the number of hypotheses in a stepwise fashion. The whole process of finding the end points of a molecule is depicted in FIG. 7, and discussed below:

1. Apply the curvature constraint

The curvature is computed along the length of the contour. Peaks are identified and ranked. Only the most prominent peaks are propagated into the next step of the process. The curvature along the contour is computed as follows: Let the contour be represented parametrically as (x(t),y(t)) and let g(t) be a Gaussian kernel. The curvature is then defined as:

$$c(t) = \frac{x'y'' - y'x''}{\sqrt{(x^2 + y^2)^3}} \quad \text{(Formula 3)}$$

where $$x' = x(t) \otimes \frac{\partial g}{\partial t} \quad x'' = x(t) \otimes \frac{\partial^2 g}{\partial^2 t}$$

$$y' = y(t) \otimes \frac{\partial g}{\partial t} \quad y'' = y(t) \otimes \frac{\partial^2 g}{\partial^2 t}$$

Some of the curvature peaks can be eliminated through the use of Curvature-Duality theorem. Leyton, *Symmetry-Curvature Duality*, COMPUTER VISION, GRAPHICS, AND IMAGE PROCESSING 327 (1987). In this context, we can check whether the axis of symmetry is inside the polygon defined by the closed contours.

2. Apply the equal length constraint

Every pair of curvature peaks should approximately divide the contour into equal lengths. This is accomplished by setting a soft threshold to accept curvature peaks for further analysis.

3. Apply the closure constraint

From a computational perspective, this is the most expensive constraint, and therefore is the final step of the computational process. This step ensures that the lines connecting the correspondence points, between each half curve, is inside the DNA object. The correspondence points are the points equidistant from the axis of symmetry. With this constraint, we can select a pair of points that correspond to end points of the DNA.

The present invention detects, tracks and performs shape representation of tubular objects. One final result was the dynamic analysis of DNA molecules being stretched by an electric field, which demonstrates that they behave much like a spring or a helix under excitation. This insight enables manipulation of a molecule in a gel under forces of an applied electric field.

Complete Automation

For complete automation of the system, the multicomputer system 24 must also determine a preferred location of the second position of the object 10, what change is necessary in the electric field for moving the object 10 from the first position to the preferred second position, and then change the electric field in accordance with the determined change.

Chamber

Figure 8:
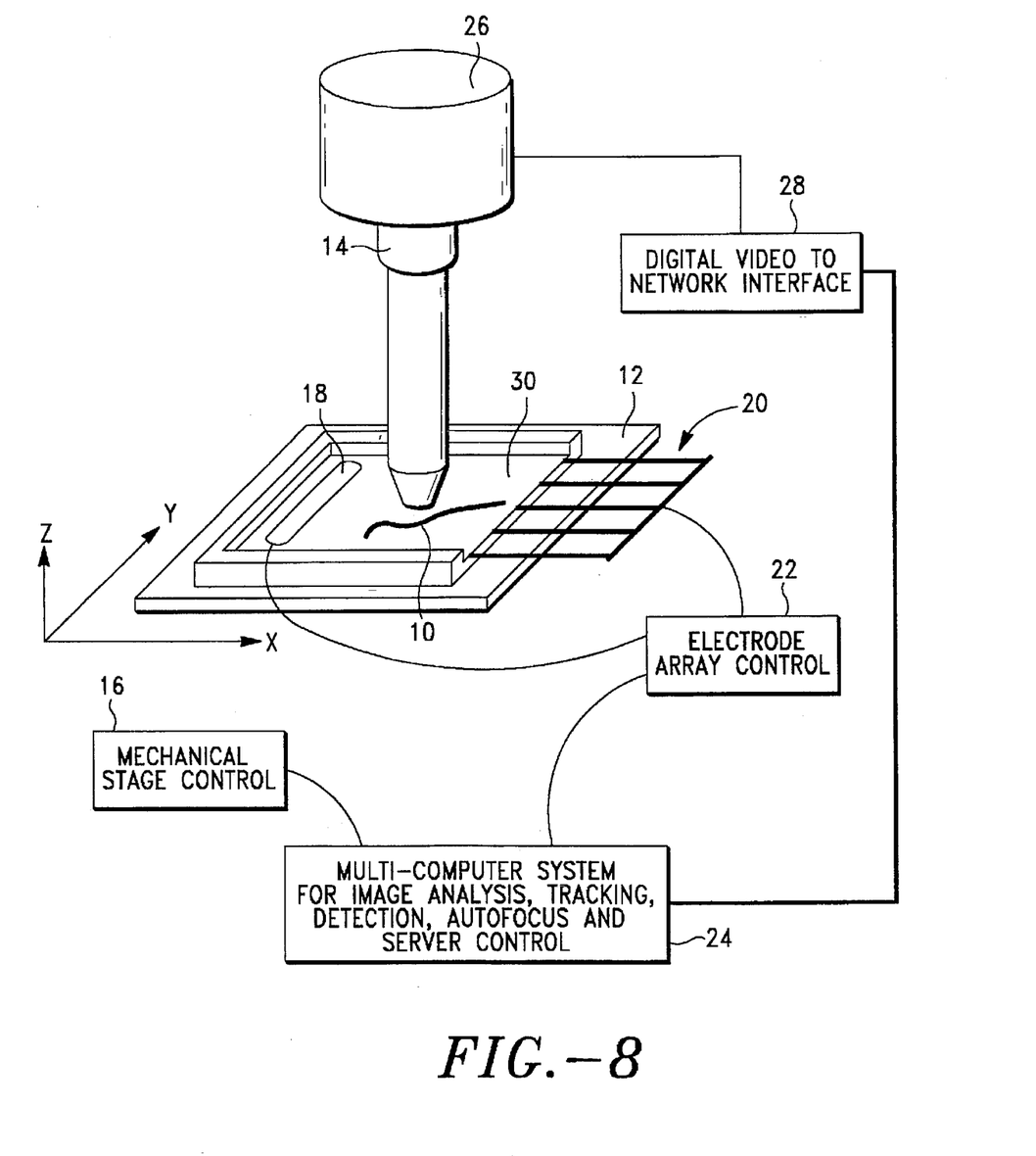
FIG. 8 is a simplified perspective view of an alternate embodiment of the invention, wherein the plurality of electrodes are positioned inside a chamber on the stage.

In another embodiment of the method and apparatus for manipulation of an object 10 on a microscope stage 12, the electrode array may be coupled as in FIG. 8, wherein a chamber 30 to hold the object to be manipulated is placed on the stage 12. The chamber 30 can be a type of gel box used in a lab for electrophoresis.

Figure 9:
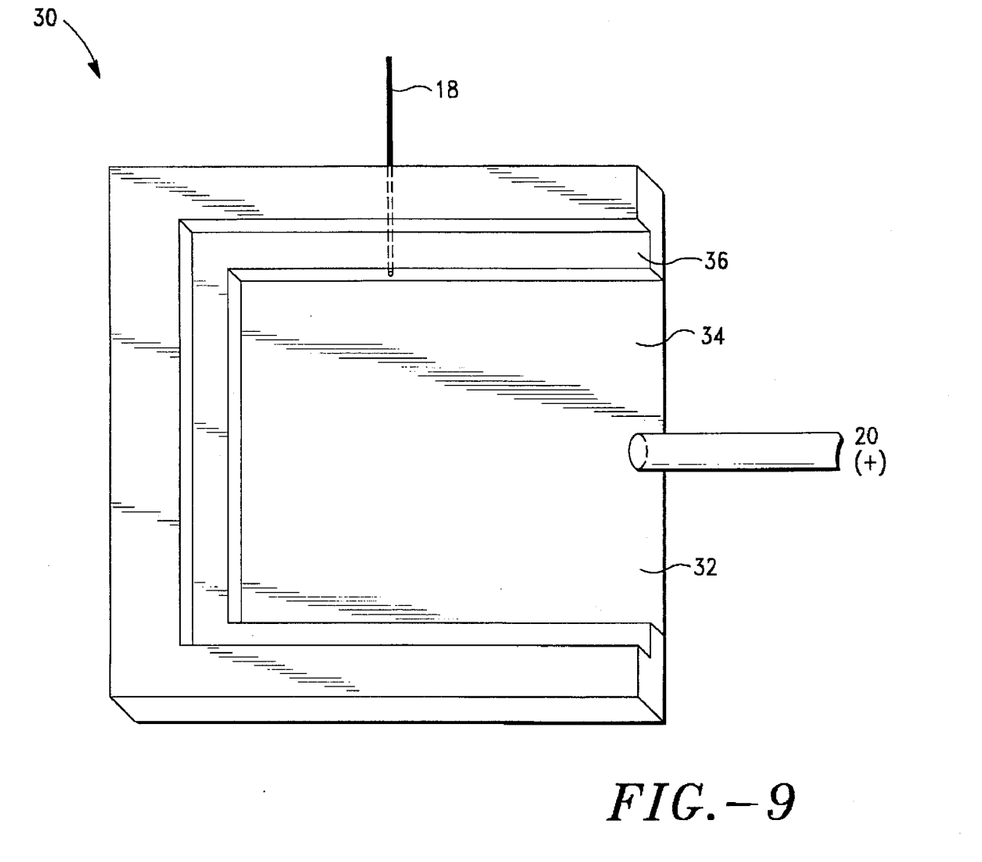
FIG. 9 is a simplified top view of an embodiment of a chamber.
Figure 10:
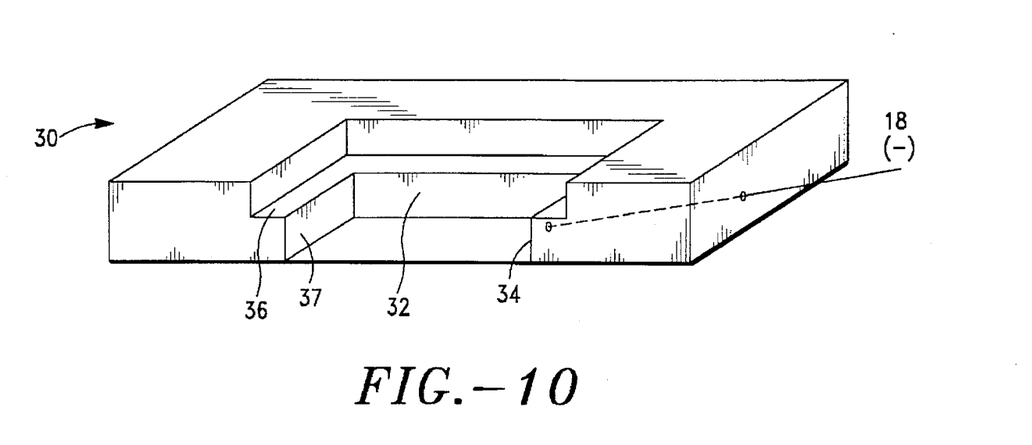
FIG. 10 is a simplified side view along the arrow 9—9 designating the opening and shelf of the chamber of FIG. 8.

Alternatively, the chamber 30 may be made in the laboratory machine shop specifically for the type of microscope used. For example, for an upright microscope, a piece of plastic suitable for use on a stage can be used. The dimensions may be about 10 cm long, 6 cm wide and 0.5 cm thick. FIGS. 9 and 10 illustrate an interior 32 of the chamber for holding and manipulating the object 10, which can be formed by hollowing part of the center of the piece of plastic. The interior 32 may have one side open 34 to receive an electrode 20 and/or to receive an end of one or more of a plurality of tubes discussed in the following paragraphs. The interior 32 has a shelf 36 to rest a cover slip (not shown), whereby, when the cover slip is placed on the shelf 36, the coverslip forms an upper limit of the opening 34, which may be about 150 to 500 microns high.

The plurality of electrodes may be coupled to the chamber 30 or positioned inside the chamber 30, as opposed to being coupled to the stage 12. When the interior 32 chamber 30 is filled with a fluid, the plurality of electrodes will become immersed. The type of fluid will depend on the object 10 to be moved. If chamber 30 comprises an opening 34, surface tension will keep the fluid from flowing out of the chamber 30.

A method for manipulating an object 10 in accordance with the above embodiment comprises the steps of filling the chamber 30 with the appropriate fluid, placing the object 10 in the chamber 30 on the stage 12, the object 10 being located at a first position, manipulating the electrode array control 22 for creating a change in the electric field, whereby changing the electric field causes the object 10 in the chamber 30 on the stage 12 to move from the first position to a preferred second position.

Nucleic Acid Manipulation

If the object 10 is a type of nucleic acid, appropriate modifications of the method and apparatus must be made. For example, the fluid must be a type of buffer for offsetting a reaction of the nucleic acid placed in the buffer, for example, commonly used buffers are 1× TE or 1× TAE, the formulas for which can be found in molecular biology procedure manuals. The microscope 14 may be a typical imaging device that operates at the extreme limits of the optical system and the photo conversion limits of the receptor system, for example, an epi-fluorescence microscope.

Figure 11:
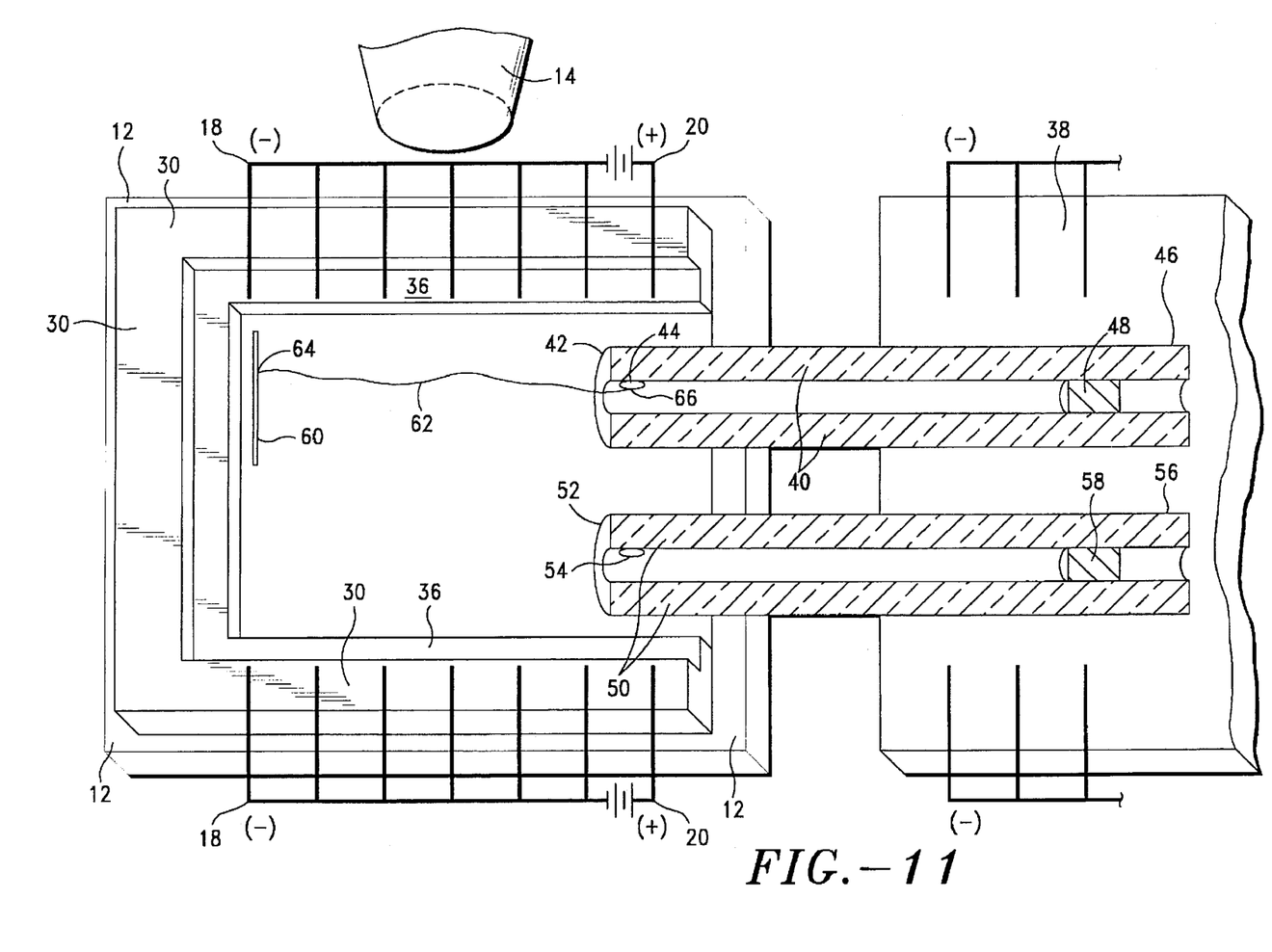
FIG. 11 is a simplified perspective and cross-sectional view of an apparatus for DNA manipulation and sectioning using the present invention.

FIG. 11 illustrates a particular method of use for manipulation of a nucleic acid across a microscope stage 12: fast, direct DNA manipulation and sectioning. This method further includes the steps of providing a micropositioning stage 38, adjacent to the stage 12, and providing a plurality of tubes positioned on top of the micropositioning stage 38 in a predetermined order. The plurality of tubes can be microcapillary tubes and each has two ends. FIG. 11 is a cross-sectional view of two tubes 40 and 50 for viewing the objects inside the tubes. Tube 40 has two ends, a first end 42 removably placed into the chamber 30 for surrounding at least part of the object on the stage. The first end 42 has an endonuclease or restriction enzyme 44 attached inside the first end 42, and a second end 46 has a plug 48. The plug 48 can be a typical agarose gel plug. The micropositioning stage 38 has a mechanical micropositioning stage control (not shown). The micropositioning stage control is electrically connected to the micropositioning stage 38 for manipulating the micropositioning stage 38, and the micropositioning stage control is electrically connected to, and is responsive to, the processing unit 24 for directing the micropositioning stage control to position the first end of one of the plurality of tubes on the micropositioning stage 38 to surround at least part of the object 10 on the stage 12.

A second set of a plurality of electrodes (not shown) is coupled to the micropositioning stage 38 for creating a second electric field through the plurality of tubes. A second electrode array control (not shown) is provided for manipulating the second electric field. If the system is automated, the second electrode array control is electrically connected to, and controlled by, the multi-computer system 24.

A substrate 60 that does not move in the first electric field, and is complimentary to various sites of nucleic acids for metal coordination is provided. Substrate 60 may, for example, be a complex with metal, glass, or quartz surfaces.

A single specific DNA molecule 62 having two ends is provided.

In general, a "molecule" is a combination of atoms into a unit in which the forces holding the atoms together within the unit are much larger than the forces between atoms in different units. For the purposes of this disclosure, a "DNA molecule" is a specific piece of a single DNA molecule used in the method of manipulating an object on a microscope stage, which can be sectioned into "fragments." Although fragments of a DNA molecule are also molecules, for the purposes of clarity in this disclosure, the sectioned fragments of the original specific piece of DNA molecule are referred to as "fragments."

A first end 64 of the specific DNA molecule 62 is attached to the substrate 60. Several methods of attachment are possible.

For example, one method of attachment was presented at the NATO Advanced Research Workshop, held in Hungary, in August of 1994. The corresponding unpublished paper is submitted herewith in the information disclosure statement and is herein incorporated by reference. This method capitalizes on a particular trait of DNA bases: that they have various sites for metal coordination, such as non-bonding electrons on nitrogen atoms and phosphate-oxygen sites.

The method anchors the first end 64 of the single specific lambda-DNA molecule 62 to a glass surface in order to image this single specific DNA molecule. The specific DNA molecule can be imaged with an appropriate medium, e.g. ethidium bromide or YoYoI iodide (491/509) (1,1'-(4,4,7,7-Tetramethyl-4,7-Diazaundecamemylene)-bis-4-[3-methyl-2,3-dihydro-(benzo-1,3-oxazole)-2-methylidene]-quinolinium tetraiodide) on an epi-fluorescence microscopic stage. To anchor the single specific lambda-DNA, selectively bind a Cp*Rh aqua ($\eta^5$-pentamethylcyclopentadienyl) rhodium ([Cp*Rh(H$_2$O)$_3$]$^{2+}$) aqua complex to a single strand 24 base oligonucleotide (24 mer) that has part of its sequence complimentary to the terminal sequence of the specific lambda-DNA 12 mer, with the Cp*Rh aqua complex bound to a selective portion (dA$_{12}$) of the 24 mer and, simultaneously to the glass/electrode surface, but not directly to the specific lambda-DNA. This reaction occurs in a buffer solution at pH 7.0, or may occur in water. All reactions are in-situ.

A second method of attaching the specific DNA molecule to the substrate is to use standard biotin-avidin techniques found in current molecular biology laboratory manuals.

A third method of attaching the specific DNA molecule to the substrate is to coat the substrate with a protein, for example, serum albumin. Protocols for this method are also found in current molecular biology laboratory manuals.

Next, the substrate 60 with the specific DNA molecule 62 attached is placed on the stage in a way to be manipulated. For example, it can be placed in the fluid filled chamber 30. The first electric field is applied through the chamber 30. Because the substrate 60 will not move in the electric field, the attached end 64 of the specific DNA molecule 62 will not move in the electric field. However, the rest of the specific DNA molecule 62 will stretch toward the micropositioning stage 38. The location of a second end 66 of the specific DNA molecule 62 is detected by looking through the microscope 14 or by the automatic detection by the multi-computer system 24 from information obtained in the image from the imaging device 26.

The location of the first end 42 of the first tube 40 mounted on the micropositioning stage 38 is detected by looking through the microscope or by visual servoing. For DNA sequencing, this is the preferred second location.

The mechanical micropositioning stage control is changed in such a way to cause the position of the micropositioning stage 38 to move so that the first end 42 of the first tube 40 surrounds the second end 66 of the specific DNA molecule 62. This can be done manually while looking through the microscope 14 or by visual servoing. Visual servoing uses the information from the image of the stage to automatically detect the physical location of the molecule, and to accurately position the first end 42 of the first tube 40 to surround the second end 66 of the specific DNA molecule 62.

Cutting the specific DNA molecule 62 and retrieving the fragment are accomplished by changing the first electric field of the stage 12 near the positive electrode tips 20. This change will cause the second end 66 of the specific DNA molecule 62 to move to a new preferred second position: in contact with the endonuclease or restriction enzyme 44 inside the first end 42 of the first tube 40, whereby the endonuclease or restriction enzyme 44 cuts off a first fragment of the second end 66 of the specific DNA molecule 62. (Although fragments of a DNA molecule are also molecules, for the purposes of clarity in this disclosure, the sectioned fragments of the original specific DNA molecule are referred to as "fragments.")

The second electric field of the micropositioning stage 38 is applied, thereby causing the first fragment to move into the plug 48 in the second end 46 of the first tube 40.

The location of the newly-cut second end 66 of the specific DNA molecule 62 is detected. This can be done by viewing through the microscope 14, or automatically by visual servoing.

The location of the first end 52 of a second tube 50 mounted on the micropositioning stage 38 is detected, either manually or by visual servoing.

The mechanical micropositioning stage control is changed, in such a way to cause the position of the micropositioning stage 38 to move so that the first end 52 of the second tube 50 surrounds the second end 66 of the specific DNA molecule 62. This can be done manually or by visual servoing.

The first electric field of the stage 12 is changed near the positive electrode tips 20, thereby causing the second end 66 of the specific DNA molecule 62 to contact the endonuclease or restriction enzyme 54 inside the first end 52 of the second tube 50, whereby the endonuclease or restriction enzyme 54 cuts off a second fragment of the second end 66 of the specific DNA molecule 62. This can be done manually or by visual servoing.

The second electric field of the micropositioning stage 38 is applied, thereby causing the second fragment to move into the plug 58 in the second end 56 of the second tube 50.

The last five steps are repeated until the specific DNA molecule 62 has been entirely cut and manipulated into the plugs in the plurality of tubes in the predetermined order.

After the specific DNA molecule has been sectioned and kept in the predetermined order, many other manipulations are possible. For example, to utilize these fragments for sequencing, each must be amplified. Toward that end, (1) a plurality of containers (not shown) are provided in the predetermined order. (2) The containers each have an amplification mixture. These containers may be eppendorf microtubes. The amplification mixture may be for amplification by polymerase chain reaction (PCR). PCR was devised in the mid-1980's and is now a standard technique in thousands of molecular biology laboratories. PCR produces enormous numbers of copies of a specified DNA sequence without resorting to other time consuming techniques, for example, cloning. Current molecular biology laboratory manuals have protocols for PCR techniques.

(3) The plugs are transferred in the predetermined order to the containers in the predetermined order for amplification. If the plugs are made of agarose, then the concentration of the agarose may depend on the type of amplification used.

(4) After the fragments of the specific DNA molecule 62 in plugs are transferred in the predetermined order, they are simultaneously amplified in the predetermined order. If amplification is by PCR, then the DNA fragment may remain in the plug because PCR does not require highly purified DNA.

Finally, the amplified fragments of the DNA molecule 62 are simultaneously sequenced in the predetermined order.

The method of DNA sequencing utilizing the manipulation of a nucleic acid across a microscope stage 12 as described above and illustrated in FIG. 11 can be accomplished with more than one copy of the specific DNA molecule 62. For example, if the first fragments of several copies of the specific DNA molecule 62 are manipulated into the first plug 48, and the second fragments of several copies of the specific DNA molecule 62 are manipulated into the second plug 58, etc., then the accuracy of amplification of the fragments in the containers may be increased. PCR can be used to amplify sequences from a single specific DNA molecule 62, however, for optimal amplification, approximately ten copies of the specific DNA molecules 62 are preferred. Multiple copies of the specific DNA fragments for amplification by PCR minimizes misincorporations of nucleotides in the PCR process and increases the signal to noise ratio.

The crucial aspect of the visualized sectioning process is that the order of each of the specific DNA fragments obtained is maintained. Therefore, the ambiguities that occur with the present shot gun cloning technique are obviated because there are no unordered fragments of the chromosomes. This novel approach could decrease the sequencing time by a factor that depends on the number of DNA fragments into which the original specific DNA molecule 62 was cut. The number of fragments increases the rate of sequencing. The rate limiting step is the number of labs available to actually sequence each of the amplified fragments. Thus a very large specific DNA molecule 62 can be conveniently cut into ordered fragments instead of having a serial effort to deconvolute a very large number of pieces on the original intact specific DNA molecule 62.

Alternate Embodiment

In another embodiment of the method and apparatus for manipulation of an object 10 on a microscope stage 12, the electrode array may be coupled to the metal clips on the stage 12 that are used for holding microscope slides.

While the foregoing detailed description has described several embodiments of the method and apparatus for manipulation of an object on a microscope stage in accordance with this invention, it is to be understood that the above description is illustrative only and not limiting of the disclosed invention. Particularly included is a device and method in accordance with this invention that provides a means for an accurate manner for further manipulations and reactions. It will be appreciated that various other embodiments fall within the scope and spirit of this invention. Thus the invention is to be limited only by the claims as set forth below.

What is claimed is:

1. An apparatus for manipulation of an object on a microscope stage comprising:

a microscope having a stage;

a plurality of electrodes coupled to the stage for creating an electric field across the stage, the electric field having at least one changeable parameter;

an electrode array control coupled to the plurality of electrodes for manipulating the electric field;

at least one processing unit, the processing unit being electrically connected to the electrode array control, the electrode array control being responsive to the processing unit;

an imaging device electrically connected to the microscope for creating an image of the stage, the imaging device being electrically connected to the processing unit for sending the image of the stage to the processing unit; and the processing unit having the ability to receive the image, detect the first position of the object on the stage, detect the preferred second position of the object on the stage, and determine how to change the electrode array control for changing the electric field to move the object from the first position to the preferred second position, wherein when the image from the imaging device is received by the processing unit, the processing unit detects the location of the object, determines how to change the electrode array control for changing the electric field to move the object from the first position to the preferred second position and changes the electric field thereby moving the object from the first position to the preferred second position.

2. The apparatus of claim 1 wherein the plurality of electrodes are coupled to the stage in an array for allowing distinct manipulations of the electric field for accurate manipulations of the object.

3. The apparatus of claim 2 further including a chamber on the stage to hold the object, the chamber having an interior, the plurality of electrodes being coupled to the chamber, wherein changing the electric field causes the object in the chamber to move from a first position to the preferred second position.

4. The chamber of claim 3 having an opening, the opening having an upper limit.

5. The chamber of claim 4 further comprising a shelf in the interior of the chamber to rest a coverslip, the shelf being positioned so that when the cover slip is placed on the shelf, the coverslip forms the upper limit of the opening.

6. The chamber of claim 5 wherein the opening is about 150 to 500 microns high to receive one or more of the plurality of electrodes on the micropositioning stage.

7. The apparatus of claim 6 further including:

a micropositioning stage adjacent to the stage;

a plurality of tubes positioned on top of the micropositioning stage in a predetermined order, each of the plurality of tubes having two ends, a first end of the plurality of tubes being in a position for surrounding at least part of the object on the stage; and a micropositioning stage control, the micropositioning stage control being electrically connected to the micropositioning stage for manipulating the micropositioning stage, and the micropositioning stage control being electrically connected to the processing unit, the micropositioning stage control being responsive to the processing unit for directing the micropositioning stage control to position the first end of one of the plurality of tubes on the micropositioning stage to surround at least part of the object on the stage, whereby when the image from the imaging device is received by the processing unit, the processing unit detects the location of the object and directs the micropositioning stage control to position the end of one of the plurality of tubes on the micropositioning stage to surround at least part of the object on the stage, thereby positioning the end of one of the plurality of tubes on the micropositioning stage to surround at least part of the object on the stage.

8. The apparatus of claim 3 further including a substrate placed on the stage which does not move in the electric field, the substrate being complimentary to various sites of nucleic acids for metal coordination.

9. An apparatus for manipulation of an object on a microscope stage comprising:

a microscope having a stage;

a chamber for holding the object, the chamber being on the stage;

a plurality of electrodes coupled to the chamber for creating an electric field across the chamber, the electric field having at least one changeable parameter, the plurality of electrodes being coupled to the chamber in an array for allowing distinct manipulations of the electric field;

an electrode array control coupled to the plurality of electrodes for manipulating the electric field;

at least one processing unit, the processing unit being electrically connected to the electrode array control, the electrode array control being responsive to the processing unit;

an imaging device electrically connected to the microscope for creating an image of the chamber, the imaging device being electrically connected to the processing unit for sending the image of the chamber to the processing unit; and the processing unit having the ability to receive the image, detect the first position of the object in the chamber, detect the preferred second position of the object in the chamber, and determine how to change the electrode array control for changing the electric field to move the object from the first position to the preferred second position, wherein when the image from the imaging device is received by the processing unit, the processing unit detects the location of the object, determines how to change the electrode array control for changing the electric field to move the object from the first position to the preferred second position and changes the electric field thereby moving the object from the first position to the preferred second position.

10. The apparatus of claim 9 further including:

a micropositioning stage adjacent to the stage;

a plurality of tubes positioned on top of the micropositioning stage in a predetermined order, each of the plurality of tubes having two ends, a first end of the plurality of tubes being in a position for surrounding at least part of the object in the chamber; and a micropositioning stage control, the micropositioning stage control being electrically connected to the micropositioning stage for manipulating the micropositioning stage, and the micropositioning stage control being electrically connected to the processing unit, the micropositioning stage control being responsive to the processing unit for directing the micropositioning stage control to position the first end of one of the plurality of tubes on the micropositioning stage to surround at least part of the object in the chamber, wherein when the image from the imaging device is received by the processing unit, the processing unit detects the location of the object and directs the micropositioning stage control to position the end of one of the plurality of tubes on the micropositioning stage to surround at least part of the object in the chamber, thereby positioning the end of one of the plurality of tubes on the micropositioning stage to surround at least part of the object in the chamber.

11. The apparatus of claim 10 further including a substrate placed in the chamber which does not move in the electric field, the substrate being complimentary to various sites of nucleic acids for metal coordination.

12. An apparatus for manipulation of a nucleic acid having two ends on a microscope stage comprising:

a microscope having a stage;

a chamber for holding the nucleic acid, the chamber being on the stage;

a plurality of electrodes coupled to the chamber for creating an electric field across the chamber, the electric field having at least one changeable parameter, the plurality of electrodes being coupled to the chamber in an array for allowing distinct manipulations of the electric field;

an electrode array control coupled to the plurality of electrodes for manipulating the electric field;

at least one processing unit, the processing unit being electrically connected to the electrode array control, the electrode array control being responsive to the processing unit;

an imaging device electrically connected to the microscope for creating an image of the chamber, the imaging device being electrically connected to the processing unit for sending the image of the chamber to the processing unit;

the processing unit having the ability to receive the image, detect the first position of the nucleic acid in the chamber, detect the preferred second position of the nucleic acid in the chamber, and determine how to change the electrode array control for changing the electric field to move the object from the first position to the preferred second position;

a micropositioning stage adjacent to the stage;

a plurality of tubes positioned on top of the micropositioning stage in a predetermined order, each of the plurality of tubes having two ends, a first end of the plurality of tubes being in a position for surrounding a free end of the nucleic acid in the chamber;

a micropositioning stage control, the micropositioning stage control being electrically connected to the micropositioning stage for manipulating the micropositioning stage, and the micropositioning stage control being electrically connected to the processing unit, the micropositioning stage control being responsive to the processing unit for directing the micropositioning stage control to position the first end of one of the plurality of tubes on the micropositioning stage to surround at least part of the nucleic acid in the chamber; and a substrate placed in the chamber which does not move in the electric field, the substrate being complimentary to various sites of the nucleic acid for metal coordination, for attaching to one end of the nucleic acid wherein when the image from the imaging device is received by the processing unit, the processing unit detects the location of the nucleic acid attached to the substrate, determines how to change the electrode array control for changing the electric field to stretch the free end of the nucleic acid away from the substrate and changes the electric field thereby stretching the nucleic acid, the processing unit then directs the micropositioning stage control to position the end of one of the plurality of tubes on the micropositioning stage to surround the free end of the nucleic acid in the chamber, thereby positioning the end of one of the plurality of tubes on the micropositioning stage to surround the free end of the nucleic acid in the chamber.

* * * * *